United States Patent [19]

Robsein et al.

[11] Patent Number: 5,260,489

[45] Date of Patent: Nov. 9, 1993

[54] PURIFICATION OF HALOGENATED AROMATIC SULFONES OR KETONES

[75] Inventors: Rex L. Robsein; Jimmie J. Straw; Darryl R. Fahey, all of Bartlesville, Okla.

[73] Assignee: Phillips Petroleum Company, Bartlesville, Okla.

[21] Appl. No.: 953,362

[22] Filed: Sep. 30, 1992

[51] Int. Cl.$^5$ .................. C07C 315/06; C07C 45/61
[52] U.S. Cl. .................................. 568/34; 568/31; 568/316; 568/332
[58] Field of Search ............... 568/34, 31, 316, 332

[56] References Cited

U.S. PATENT DOCUMENTS

| | | | |
|---|---|---|---|
| 3,770,832 | 11/1973 | Leslie et al. | 260/607 |
| 4,303,776 | 12/1981 | Baron et al. | 528/171 |
| 4,990,678 | 2/1991 | Herd et al. | 568/34 |
| 5,081,306 | 1/1992 | Knox | 568/34 |

FOREIGN PATENT DOCUMENTS

354954A1  1/1990  European Pat. Off. .

Primary Examiner—Marianne M. Cintins
Assistant Examiner—Margaret J. Page
Attorney, Agent, or Firm—Lucas K. Shay

[57] ABSTRACT

A process for purifying a halogenated aromatic sulfone or ketone compound comprises contacting the compound with a mixture containing a solvent having a normal boiling point less than about 225° C. and water to form a second mixture, heating the second mixture at a temperature sufficient to substantially dissolve the halogenated compound to form a third mixture, cooling the third mixture to purify and recrystallize the compound, and recovering the purified, recrystallized compound. A second embodiment of the invention comprises repeating the purification process steps at least once to further purify the halogenated aromatic sulfone or ketone compound.

19 Claims, No Drawings

PURIFICATION OF HALOGENATED AROMATIC SULFONES OR KETONES

FIELD OF THE INVENTION

This invention relates to a process for purifying halogenated aromatic sulfone or ketone compounds.

BACKGROUND OF THE INVENTION

Halogenated aromatic sulfone or ketone compounds can be produced by the Lewis-acid catalyzed condensation of a halogenated aromatic compound containing sulfonyl or carbonyl groups with an aromatic hydrocarbon. For example, 4,4'-bis(p-chlorophenylsulfonyl)biphenyl can be produced by reacting p-chlorobenzenesulfonyl chloride with biphenyl using nitrobenzene as a solvent in the presence of a Lewis acid catalyst such as ferric chloride or aluminum chloride. Compared with aluminum chloride, ferric chloride is a preferred catalyst because it displays both high activity and product selectivity. The crude 4,4'-bis(p-chlorophenylsulfonyl)biphenyl product mixture contains unreacted p-chlorobenzenesulfonyl chloride, bis(p-chlorophenyl)sulfone which is an impurity in the p-chlorobenzenesulfonyl chloride, 4-(p-chlorophenylsulfonyl)biphenyl which is the monohalophenylsulfonyl-substituted product, and inorganic impurities such as, for example, iron-containing compounds when ferric chloride is used as catalyst. It has been found that in scaling-up this preparation of the aromatic sulfone or ketone compounds, the iron content in the product mixture is increased.

Halogenated aromatic sulfone or ketone compounds can be used in a variety of applications. For example, the halogenated aromatic sulfone or ketone compounds can be used as monomers in the production of high-temperature arylene sulfide sulfone and arylene sulfide ketone polymers.

When the halogenated aromatic sulfone or ketone compounds are used as monomers for arylene sulfide polymers, these side products act as chain terminators during polymerization and therefore must be removed. Furthermore, the iron contaminant interferes with the polymerization process for preparing the arylene sulfide polymers from the monomers as well as imparts color to and changes physical properties of the resulting arylene sulfide polymers. Therefore, it is necessary to purify the halogenated aromatic sulfone or ketone compounds.

Purification of the desired halogenated aromatic sulfone or ketone compounds has been a problem due to low solubility in most organic solvents and the very similar solubility of undesirable monohalo-substituted reaction products. Traditional recrystallization processes can produce high purity halogenated aromatic sulfone or ketone compounds, but they have the disadvantages of low throughput, difficulty in removing residual solvent, and difficulty in scaling to pilot plant or commercial operations. Therefore, a purification process which is economical, commercially viable, and can utilize inexpensive solvents to produce high purity product with good yield is highly desirable.

SUMMARY OF THE INVENTION

An object of the invention is to provide a process for purifying halogenated aromatic sulfone or ketone compounds. A further object of the invention is to provide an efficient, commercially viable and economical process to purify halogenated aromatic sulfone or ketone compounds. Still a further object of the invention is to provide a process to purify halogenated aromatic sulfone or ketone compounds for use, such as, for example, as monomers in the production of high-temperature arylene sulfide sulfone and arylene sulfide ketone polymers. Other objects, advantages and features will become more apparent as the invention is more fully described.

According to the invention, a process for purifying a compound having a general formula of X—Ar—Y—Ar'—Y—Ar—X, wherein each X is a halogen, Y is —$SO_2$ or —CO—, and Ar and Ar' can be the same or different and are each an aromatic radical of 6 to 14 carbon atoms, comprises: (1) contacting the compound with a mixture comprising a solvent having a normal boiling point less than about 225° C. and water to form a second mixture; (2) heating the second mixture to a temperature that is sufficient to substantially dissolve the compound to form a third mixture; (3) cooling the third mixture to recrystallize the compound whereby a purified and recrystallized compound is formed; and (4) recovering the purified and recrystallized compound.

DETAILED DESCRIPTION OF THE INVENTION

The process of the invention comprises contacting a compound having the formula of X—Ar—Y—Ar'—Y—Ar—X, wherein each X is a halogen, Y is selected from the group consisting of —$SO_2$ and —CO—, and Ar and Ar' can be the same or different and are each an aromatic radical of 6 to 14 carbon atoms with a mixture comprising a solvent and water to form a second mixture, heating the mixture to a temperature that is sufficient to substantially dissolve the compound to form a third mixture, cooling the third mixture to recrystallize the compound whereby a purified and recrystallized compound is formed, and recovering the purified and recrystallized compound.

The crude, halogenated aromatic sulfone or ketone compound can optionally be washed with a solvent prior to purification of the halogenated aromatic sulfone or ketone compound to remove residual solvent used during the production of the halogenated aromatic sulfone or ketone compound. Suitable washing solvents are those applicable in the invention.

Applicable halogenated aromatic sulfone or ketone compounds are those which are not very soluble in typical recrystallization solvents at ambient temperatures (about 25° C.). Examples of suitable halogenated aromatic sulfones or ketones having the formula of X—Ar—Y—Ar'—Y—Ar—X include, but are not limited to,
4,4'-bis(p-chlorophenylsulfonyl)biphenyl,
4,4'-bis(p-bromophenylsulfonyl)biphenyl,
4,4'-bis(p-fluorophenylsulfonyl)biphenyl,
1,4-bis(p-chlorophenylsulfonyl)benzene,
1,4-bis(p-fluorophenylsulfonyl)benzene,
1,4-bis(p-fluorobenzoyl)benzene,
4,4'-bis(p-chlorobenzoyl)biphenyl,
4,4'-bis(p-bromobenzoyl)biphenyl,
1,4-bis(p-chlorobenzoyl)benzene,
2,6-bis(p-chlorophenylsulfonyl)naphthalene,
2,6-bis(p-chlorobenzoyl)naphthalene,
and other similar compounds. The preferred halogenated aromatic sulfones or ketones are
4,4'-bis(p-chlorophenylsulfonyl)biphenyl and
4,4'-bis(p-chlorobenzoyl)biphenyl.

Applicable solvents for use in the invention are those that have normal boiling points less than about 225° C. preferably less than about 200° C. The most preferred solvents of the invention are those having a normal boiling point less than about 100° C. due to ease of solvent recovery and favorable economics of using it. Suitable solvents are selected from the group consisting of halogenated hydrocarbons, alcohols, ethers, esters, ketones, carboxylic acids having no more than 7 carbon atoms, lactams, amides, hydrocarbons, and mixtures thereof. Examples of suitable solvents include, but are not limited to, methylene chloride, dichloroethane, chlorobenzene, isopropanol, acetone, methyl ethyl ketone, acetic acid, benzene, toluene, xylene, N-methyl-2-pyrrolidone, N,N-dimethylformamide, and mixtures thereof. The presently most preferred solvent is methylene chloride because of easy recovery.

In a further embodiment, the applicable solvent comprises solvent recycled from a previous purification plus fresh solvent as make-up. Use of recycled solvent can increase the ultimate recovery of purified halogenated aromatic sulfone or ketone compound because such recycled solvent contains a small quantity of the compound.

The weight ratio of solvent to the halogenated aromatic sulfone or ketone compound is in the range of from about 0.5:1 to about 40:1, preferably from about 0.75:1 to about 20:1, most preferably from 1:1 to 10:1. As the weight ratio increases, the temperature required to substantially dissolve the crude, halogenated aromatic sulfone or ketone compound mixture is generally reduced.

The weight ratio of water to the halogenated aromatic sulfone or ketone compound is in the range of from 0.05:1 to about 5:1, preferably from about 0.075:1 to about 2:1, and most preferably from 0.1:1 to 1:1 to achieve best reduction in inorganic impurities.

The temperature used to substantially dissolve the halogenated aromatic sulfone or ketone compound mixture in the process of the invention is in the range of from about 50° C. to about 300° C., preferably from about 80° C. to about 250° C., and most preferably from 100° C. to 200° C. The temperature selected will be somewhat dependent upon the weight ratio of solvent to halogenated aromatic sulfone or ketone compound utilized. In addition, the time the solution is heated generally depends on the temperature used. However, if the temperature selected is too low, a long hold time will not be sufficient to obtain the desired purity. In a preferred embodiment, the mixture of halogenated aromatic sulfone or ketone compound, solvent, and water is heated for at least about 0.15 minute to about 600 minutes, preferably for at least about 1 minute, most preferably for at least 5 minutes.

The process of the invention can be carried out in any suitable purification system. It is, however, preferred that it be carried out in a closed system. The closed system of the invention is preferably a pressure vessel such as, for example, a sealed autoclave. The pressure generated during the heating step can be the vapor pressure of the system at the selected temperature or a pressure less than about 500 psig, preferably less than about 300 psig can be applied. If an applied pressure is desired, an inert gas is preferably used to pressurize the system. The inert gas includes, but is not limited to nitrogen, helium, neon, argon, and mixtures thereof. The currently preferred inert gas is nitrogen, due to low cost and ready availability.

The purified halogenated aromatic sulfone or ketone compound can be recovered by any conventional means such as, for example, filtration followed by drying.

In a further embodiment, the purified halogenated aromatic sulfone or ketone compound can be further purified by repeating the steps of contacting the halogenated aromatic sulfone or ketone compound with a mixture comprising a solvent having a normal boiling point less than about 225° C. and water to form a second mixture, heating the second mixture to a temperature that is sufficient to substantially dissolve the compound to form a third mixture, cooling the third mixture to recrystallize the compound whereby a further purified and recrystallized compound is formed, and recovering the further purified and recrystallized compound. Additional recrystallizations may be necessary depending upon the purity of the starting material, desired product purity, and solvent selected.

In a further embodiment, the purified halogenated aromatic sulfone or ketone compound can be washed with a washing solvent to remove the recrystallization solvent from the purified product during product recovery. Suitable washing solvents are those which are applicable for use in the invention. The preferred solvent for washing is acetone, due to its high volatility, favorable economics, and availability.

EXAMPLES

In the following examples, the purity of the monomer was determined by high pressure liquid chromatography (HPLC) as well as judged by production of a high quality polyphenylene sulfide sulfone copolymer. Polyphenylene sulfide sulfone copolymer flow rates were determined by the method of ASTM D-1238, Condition 360/5.0, modified to use a five minute preheat. The value of flow rate is expressed as grams per ten minutes (g/10 min).

The extrudates from the flow rate determinations were rated for quality in terms of gassiness (internal voids), color, clarity, and surface smoothness. Numerical ratings were given for each extrudate using a scale of 1 to 4 with 1 being the best and 4 being the worst. A polymer with ratings of 1/1/1/1 for gas/color/clarity/surface has very good melt stability (very good extrudate quality) under the flow rate conditions, while a polymer with ratings of 4/4/4/4 would have very poor melt stability (very poor extrudate quality).

Copolymer inherent viscosities (I.V.) were determined at 30° C. with solutions containing 0.5 grams of polymer per 100 milliliters (mL) of N-methyl-2-pyrrolidone (NMP). The units of I.V. are deciliters per gram (dL/g).

Copolymer ash values were determined by burning a weighed sample of the polymer in a platinum dish. Residual carbonaceous material was removed by heating the platinum dish and contents at 540° C. in a muffle furnace. The weight of the residue (ash) is expressed as a percentage of the original weight (wt %) of the copolymer.

Iron levels, in units of parts per million (ppm) iron, in the monomers were determined by inductively coupled plasma-mass spectroscopy.

4,4'-Bis(p-chlorophenylsulfonyl)biphenyl monomer purities were determined by high pressure liquid chromatography with a Waters chromatography system using methylene chloride as solvent.

EXAMPLE I

This example illustrates the synthesis and a partial purification of 4,4'-bis(p-chlorophenylsulfonyl)biphenyl (BCPSB) in a large reactor.

A 1136 liter (L), glass-lined, stirred reactor was purged with nitrogen and charged with 210 kg of p-chlorophenylsulfonyl chloride, 68 kg of biphenyl, 360 g of ferric chloride, and 181 kg of nitrobenzene. After the reactor had been pressured to 69 kPa with nitrogen and heated to 50° C., the stirrer was started and the mixture was heated to 140° C. at 0.5° C./min. The mixture was stirred at 140° C. for 5 hours and then cooled to 80° C. Hydrochloric acid fumes emitted from the reaction were scrubbed by a dilute solution of sodium hydroxide having a pH of at least 11.

Following a purge of the reactor with nitrogen, 3 drums (189 L each) of acetone were slowly added, and the mixture was stirred for 30 minutes. The stirrer was turned off, and the mixture was allowed to stand for 30 minutes allowing a solid product to settle to the bottom of the reactor. The solvent was decanted from the solids and the treatment with acetone followed by decantation was repeated two more times.

Two drums (189 L each) of methylene chloride were added to the reactor to produce a slurry with the solid BCPSB monomer. The slurry was then transferred to a recrystallizing vessel. The reactor was flushed with methylene chloride which was also transferred to the recrystallization vessel. The mixture in the recrystallization vessel was heated to 140° C. in one hour and held for 5 minutes at 140° C. After the mixture had been cooled to 25° C. and stirred for one hour, the mixture was filtered and dried to produce BCPSB monomer. This BCPSB was designated as sample A, was used in the purification attempts described below, contained 420 ppm iron, and had a purity of 99.92% based on HPLC.

EXAMPLE II

This example illustrates the treatments of BCPSB monomer, the iron levels in the treated monomers, and the purity of the treated monomers.

A stirred, 7.6 L autoclave was charged with 1000 g of BCPSB monomer A obtained in Example I and 4 L of methylene chloride. The autoclave was purged with nitrogen and heated with stirring. After one hour the liquid temperature was 110° C. The autoclave heat was turned off after 1.5 hrs with a liquid temperature of 142° C. After the autoclave had cooled to 38° C., the product was removed, filtered, and washed with 2 L of acetone. The air-dried product, designated A1, contained 490 ppm iron. Sample A1 had a higher iron level than starting material A. The discrepancy in iron levels between A1 and A was probably due to either nonuniform distribution of iron in sample A or variation in iron analyses, or both.

In another treatment, 1000 g of BCPSB monomer A and 4 L of acetone were stirred at room temperature (about 25° C.) for 10 min, filtered, and air dried. This washed powder was charged to a 7.6 L autoclave with 4 L of methylene chloride. The autoclave was purged with nitrogen, heated to 140° C. with stirring, cooled, and the product was removed from the autoclave. The product was filtered, washed with 2 L of acetone, and air dried to yield product A2, which contained 430 ppm iron.

In the next three treatments, 1000 g of BCPSB monomer A was charged with 4 L of a solvent to the autoclave, and the autoclave was purged with nitrogen and heated to 140° C. with stirring. The autoclave was cooled and the product was removed from the autoclave. The products were filtered, washed with acetone (2 L in run A3, 4 L in A4 and A5), and air dried. Solvents used were acetone for product A3, a mixture of acetone and acetic acid (3 wt % acetic acid based on the total solvent charge) for product A4, and a mixture of methylene chloride and water (10 wt % water based on the total solvent used) for product A5.

The results of these treatments are summarized in Table I. The only procedure that significantly reduced the BCPSB iron level from the high level in the original crude sample A was the process using the methylene chloride/water mixture (i.e. invention process) to produce product A5. A second treatment with methylene chloride only (product A1) failed to reduce the iron level.

TABLE I

Monomer Purification

| BCPSB[a] Monomer | Treatment[b] | Iron ppm |
|---|---|---|
| A | Unpurified | 420 |
| A1 | Methylene Chloride | 490 |
| A2 | Acetone[c]/Methylene Chloride | 420 |
| A3 | Acetone | 390 |
| A4 | Acetone/3% Acetic Acid | 250 |
| A5[d] | Methylene Chloride/10% $H_2O$ | 50 |

[a] 4,4'-bis(p-chlorophenylsulfonyl)biphenyl.
[b] Treatment was 142° C. for 1.5 hours.
[c] Room temperature (25° C.) acetone wash.
[d] Monomer obtained by inventive process.

EXAMPLE III

For comparison purposes, a control, small scale preparation of BCPSB monomer was conducted.

BCPSB monomer B was prepared by the Friedel-Crafts sulfonylation (using 10.22 g of $FeCl_3$ as catalyst) of biphenyl (1855.1 g) with p-chlorobenzenesulfonyl chloride (5853.0 g) in nitrobenzene (4927.5 ml) in a 22 L glass reactor. The reaction conditions were the same as those described in Example I. The reaction product was cooled, filtered, and washed with methanol to produce crude BCPSB, similar to the process described in Example I.

This crude BCPSB was charged to a 7.6 L autoclave with 4 L of methylene chloride. After the autoclave had been purged with nitrogen, the autoclave was heated to 140° C. and the heat turned off. The autoclave contents were filtered and washed with acetone. Four batches of BCPSB prepared and washed by this procedure were combined to produce BCPSB monomer B, which was 99.84 wt % pure by HPLC and contained 6 ppm iron. The results show that desirably low iron levels were obtained in the small-scale preparation of BCPSB (compared to the large-scale preparation shown in Example I).

EXAMPLE IV

This example demonstrates the advantages of a recrystallization of iron-containing BCPSB from a methylene chloride-water mixture for the purification of the BCPSB monomer.

BCPSB monomers from Examples II and III were used to prepare copolymers from a 3:1:4 molar ratio of BCPSB, bis(p-chlorophenyl) sulfone, and sodium hydrosulfide, respectively, in the presence of a base.

In a typical polymerization, a stirred, 7.6 L autoclave was charged with 1.125 g-mol BCPSB, 0.375 g-mol bis(p-chlorophenyl) sulfone (BCPS), 1.5 g-mol sodium acetate (NaOAc), 3.0 g-mol sodium carbonate ($Na_2CO_3$), 10.23 g-mol deionized water, 1.456 g-mol sodium hydrosulfide (NaSH) hydrate containing 58.96 weight percent NaSH, and 12 g-mol NMP. The autoclave was purged 4 times with nitrogen, heated with stirring at 3° C. per minute to 200° C., and held for 3 hrs.

After the autoclave had been cooled to 30° C., it was opened and the autoclave contents were removed and mixed in a blender. The crude mixture was filtered, and the filter cake was washed with 4 L of deionized water. This washed filter cake was then washed 4 times with hot (90° C.) deionized water and once with room temperature (25° C.), deionized water. The copolymer was dried in a vacuum oven at 170° C. overnight. Each copolymer was tested for I.V. and ash.

Selected copolymers from the polymerization reactions were treated with aqueous zinc acetate. In a typical treatment, the dried copolymer was charged to a 7.6 L autoclave with 4 L of deionized water and one wt % (based on the copolymer weight) zinc acetate. The stirred autoclave was purged with nitrogen, heated to 185° C., held at that temperature for one hour, and then cooled. The autoclave was opened, the contents were removed and filtered, and the solid was washed with 4 L of deionized water. After the copolymer had been washed three times with hot (90° C.) deionized water (4 L each) and three times with cold (25° C.) deionized water (4 L each), the copolymer was dried overnight in a vacuum oven at 170° C. Each treated copolymer was evaluated for I.V., ash, flow rate, and extrudate quality.

Polymerization 1 is a control run with the unpurified biphenyl monomer A. Polymerizations 2 through 6 used the treated monomers A1 through A5 described in Example II. Copolymer 7 was prepared from a very pure (6 ppm iron) BCPSB monomer B from a laboratory synthesis described in Example III.

The results of the polymerizations are summarized in Table II. Copolymers 2 and 3 had high ash levels and were not treated with zinc acetate. The properties listed in Table II for copolymers 2 and 3 are for the materials without a zinc acetate treatment, and the properties of the other copolymers are for zinc acetate treated copolymers. Copolymers 1 and 4 had very poor quality extrudates. Copolymer 5 had a good quality extrudate, but the flow rate was lower than the control copolymer 1. Invention copolymer 6 had good extrudate quality similar to that of copolymer 7, which was made from a low-iron laboratory monomer.

These results demonstrate that the invention process produced highly purified BCPSB monomer and the purity of the monomer enabled high quality copolymers to be produced from it.

TABLE II

| | Copolymer Production | | | | |
|---|---|---|---|---|---|
| Copolymer | BCPSB Monomer | IV, dL/g | Ash, Wt % | Flow Rate, g/10 min | Extrudate Quality[a] |
| 1 | A | 0.41 | 0.56 | 1.1 | 4/4/4/4 |
| 2 | A1 | 0.40 | 1.23 | NR[b] | NR[b] |
| 3 | A2 | 0.43 | 0.73 | NR[b] | NR[b] |
| 4 | A3 | 0.45 | 0.60 | 0.7 | 4/4/4/4 |
| 5 | A4 | 0.44 | 0.43 | 0.5 | 1/4/1/2 |
| 6 | A5 | 0.42 | 0.52 | 1.1 | 3/4/1/3 |
| 7 | B | 0.41 | 0.25 | 0.8 | 3/3/1/3 |

[a]Extrudate quality from flow rate determination with rankings of gas/color/clarity/surface with a scale of 1 = best to 4 = worst.
[b]NR, not run (due to high ash).

The results shown in the above examples clearly demonstrate that the present invention is well adapted to carry out the objects and attain the ends and advantages mentioned as well as those inherent therein. While modifications may be made by those skilled in the art, such modifications are encompassed within the spirit of the present invention as defined by the specification and the claims.

That which is claimed is:

1. A process for purifying a compound having a general formula of X—Ar—Y—Ar'—Y—Ar—X, wherein each X is a halogen, Y is selected from the group consisting of —$SO_2$ and —CO—, and Ar and Ar' are the same or different and are each an aromatic radical of 6 to 14 carbon atoms, wherein said process comprises: (1) contacting said compound with a mixture comprising a solvent having a normal boiling point less than about 225° C. and water to form a second mixture wherein said solvent is selected from the group consisting of halogenated hydrocarbons, ethers, esters, ketones, lactams, amides, hydrocarbons, and mixtures thereof; (2) heating said second mixture to a temperature that is sufficient to substantially dissolve said compound to form a third mixture; and (3) cooling said third mixture to recrystallize said compound whereby a purified, recrystallized compound is formed.

2. A process according to claim 1 further comprising recovering said purified, recrystallized compound.

3. A process according to claim 1 wherein said compound is 4,4-'bis(p-chlorophenylsulfonyl)biphenyl.

4. A process according to claim 1 wherein said solvent is selected from the group consisting of methylene chloride, dichloroethane, chlorobenzene, acetone, methyl ethyl ketone, benzene, toluene, xylene, N-methyl-1-pyrrolidone, N,N-dimethylformamide, and mixtures thereof.

5. A process according to claim 1 wherein said solvent has a normal boiling point less than about 100° C.

6. A process according to claim 4 wherein said solvent is methylene chloride.

7. A process according to claim 1 wherein said temperature is in the range of from about 50° C. to about 300° C.

8. A process according to claim 7 wherein said temperature is in the range of from 100° C. to 200° C.

9. A process according to claim 1 wherein said heating is maintained for at least about 0.15 minute.

10. A process according to claim 9 wherein said heating is maintained for at least about 5 minutes.

11. A process according to claim 1 wherein said solvent is present in said mixture in a weight ratio of solvent to compound in the range of from about 0.5:1 to about 40:1.

12. A process according to claim 11 wherein said weight ratio is in the range of from 1:1 to 10:1.

13. A process according to claim 1 wherein said water is present in said mixture in a weight ratio of water to compound in the range of from about 0.05:1 to about 5:1.

14. A process according to claim 13 wherein said weight ratio is in the range of from 0.1:1 to 1:1.

15. A process according to claim 1 wherein said solvent and said water comprise solvent and water recycled from a previous purification plus fresh solvent and water as make-up.

16. A process according to claim 2 wherein said purified, recrystallized compound is washed with a solvent.

17. A process for purifying 4,4'-bis(p-chlorophenylsulfonyl)biphenyl comprising:

(1) contacting said 4,4'-bis(p-chlorophenylsulfonyl)biphenyl with a halogenated hydrocarbon and water to form a mixture wherein the weight ratio of said halogenated hydrocarbon to said 4,4'-bis(p-chlorophenylsulfonyl)biphenyl is in the range of from about 0.5:1 to about 40:1 and the weight ratio of said water to said 4,4'-bis(p-chlorophenylsulfonyl)biphenyl is in the range of from about 0.05:1 to about 5:1;

(2) heating said mixture at a temperature in the range of from about 50° C. to about 300° C. for at least about 0.15 minute in a closed system to form a second mixture under a pressure of less than about 500 psig;

(3) cooling said second mixture to about 25° C. to recrystallize said 4,4'-bis(p-chlorophenylsulfonyl)biphenyl to produce a purified, recrystallized 4,4'-bis(p-chlorophenylsulfonyl)biphenyl;

(4) recovering said purified, recrystallized 4,4'-bis(p-chlorophenylsulfonyl)biphenyl.

18. A process according to claim 17 wherein said halogenated hydrocarbon is methylene chloride.

19. A process according to claim 17 wherein the weight ratio of said halogenated hydrocarbon to said 4,4'-bis(p-chlorophenylsulfonyl)biphenyl is in the range of from 1:1 to 10:1; the weight ratio of said water to said 4,4'-bis(p-chlorophenylsulfonyl)biphenyl is in the range of from 0.1:1 to 1:1; and said heating in step (2) is at a temperature in the range of from 100° C. to 200° C. for at least about 5 minutes under a pressure of less than about 300 psig.

* * * * *

UNITED STATES PATENT AND TRADEMARK OFFICE
CERTIFICATE OF CORRECTION

PATENT NO.  : 5,260,489

DATED       : November 9, 1993

INVENTOR(S) : Rex L. Bobsein, Darryl R. Fahey, Jimmie Joe Straw

It is certified that error appears in the above-identified patent and that said Letters Patent is hereby corrected as shown below:

On title page, item (75) Inventor: delete "Rex L. Robsein" and insert therefor ---Rex L. Bobsein---.

Signed and Sealed this

Twenty-sixth Day of April, 1994

Attest:

BRUCE LEHMAN

*Attesting Officer*　　　*Commissioner of Patents and Trademarks*